(12) United States Patent
Limaye et al.

(10) Patent No.: US 12,285,388 B2
(45) Date of Patent: Apr. 29, 2025

(54) SYRINGE ASSEMBLY AND ADAPTER MEMBER

(71) Applicant: Becton, Dickinson and Company, Franklin Lakes, NJ (US)

(72) Inventors: Amit Uday Limaye, Wayne, NJ (US); Tianqi Hang, Orange, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 933 days.

(21) Appl. No.: 17/274,007

(22) PCT Filed: Jan. 31, 2019

(86) PCT No.: PCT/US2019/015950
§ 371 (c)(1),
(2) Date: Mar. 5, 2021

(87) PCT Pub. No.: WO2020/050875
PCT Pub. Date: Mar. 12, 2020

(65) Prior Publication Data
US 2021/0251849 A1  Aug. 19, 2021

Related U.S. Application Data

(60) Provisional application No. 62/728,458, filed on Sep. 7, 2018.

(51) Int. Cl.
A61J 1/20 (2006.01)
(52) U.S. Cl.
CPC ............. *A61J 1/201* (2015.05); *A61J 1/2051* (2015.05); *A61J 1/2096* (2013.01)

(58) Field of Classification Search
CPC ...... A61J 1/2096; A61J 1/2003; A61J 1/2006; A61J 1/2055; A61J 1/201; A61J 1/2051;
(Continued)

(56) References Cited

U.S. PATENT DOCUMENTS 5,454,409 A   10/1995  McAffer et al.
5,776,124 A    7/1998  Wald
(Continued)

FOREIGN PATENT DOCUMENTS

JP   2008-532701 A   8/2008
JP   2015-506255 A   3/2015
(Continued)

OTHER PUBLICATIONS

International Search Report dated Apr. 18, 2019, which issued in the corresponding PCT Patent Application No. PCT/US2019/015950.

*Primary Examiner* — Philip R Wiest
*Assistant Examiner* — Linnae E. Raymond
(74) *Attorney, Agent, or Firm* — Dickinson Wright PLLC

(57) ABSTRACT

A syringe assembly (10) includes a syringe barrel (12) having a proximal end and a distal end, a needle-bearing hub (20) coupled to the distal end of the syringe barrel (12). An adapter (32, 104, 120) is configured for connecting to a container containing a substance, such as a medication, drug, or pharmaceutical. The adapter has a body (54, 114, 148) with a cavity (76, 116, 160), a proximal end, and a distal end. A closure member (84, 105) is coupled to the proximal end of the body. The closure member has a thickness where a needle of a syringe can pierce the closure member to access the cavity of the body. A cannula (98, 118, 170) extends from the distal end of the body for accessing the container.

12 Claims, 13 Drawing Sheets

(58) Field of Classification Search
CPC ............... A61J 1/1481; A61J 1/2089; A61J 1/2068–2075
See application file for complete search history.

(56) References Cited

U.S. PATENT DOCUMENTS

| | | | |
|---|---|---|---|
| 7,743,799 B2* | 6/2010 | Mosler | A61J 1/2096 |
| | | | 604/405 |
| 8,852,145 B2* | 10/2014 | Denenburg | A61M 5/3294 |
| | | | 604/87 |
| 9,642,775 B2* | 5/2017 | Sanders | A61M 39/105 |
| 10,406,072 B2* | 9/2019 | Chhikara | A61M 5/31513 |
| 2009/0299325 A1 | 12/2009 | Vedrine et al. | |
| 2011/0160701 A1* | 6/2011 | Wyatt | A61J 1/2096 |
| | | | 604/406 |
| 2012/0078214 A1* | 3/2012 | Finke | A61J 1/2089 |
| | | | 604/411 |
| 2012/0179129 A1* | 7/2012 | Imai | A61J 1/2096 |
| | | | 604/414 |
| 2014/0261877 A1* | 9/2014 | Ivosevic | A61J 1/2048 |
| | | | 141/27 |
| 2015/0013810 A1 | 1/2015 | Carrel et al. | |
| 2015/0123398 A1 | 5/2015 | Sanders et al. | |
| 2015/0297460 A1* | 10/2015 | Mansour | A61M 5/31 |
| | | | 141/2 |
| 2018/0064605 A1* | 3/2018 | Noguchi | A61J 1/2048 |

FOREIGN PATENT DOCUMENTS

| | | |
|---|---|---|
| WO | WO2013115731 A1 | 8/2013 |
| WO | 2016/142369 A1 | 9/2016 |

\* cited by examiner

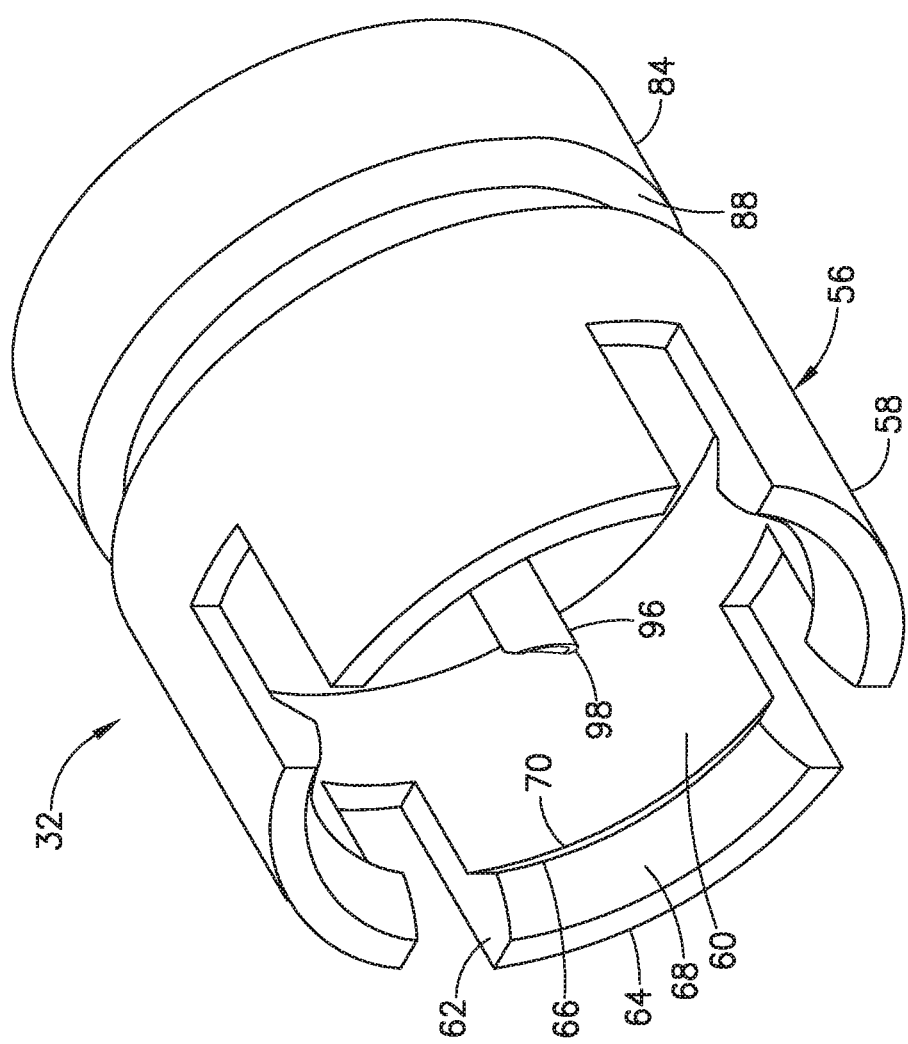

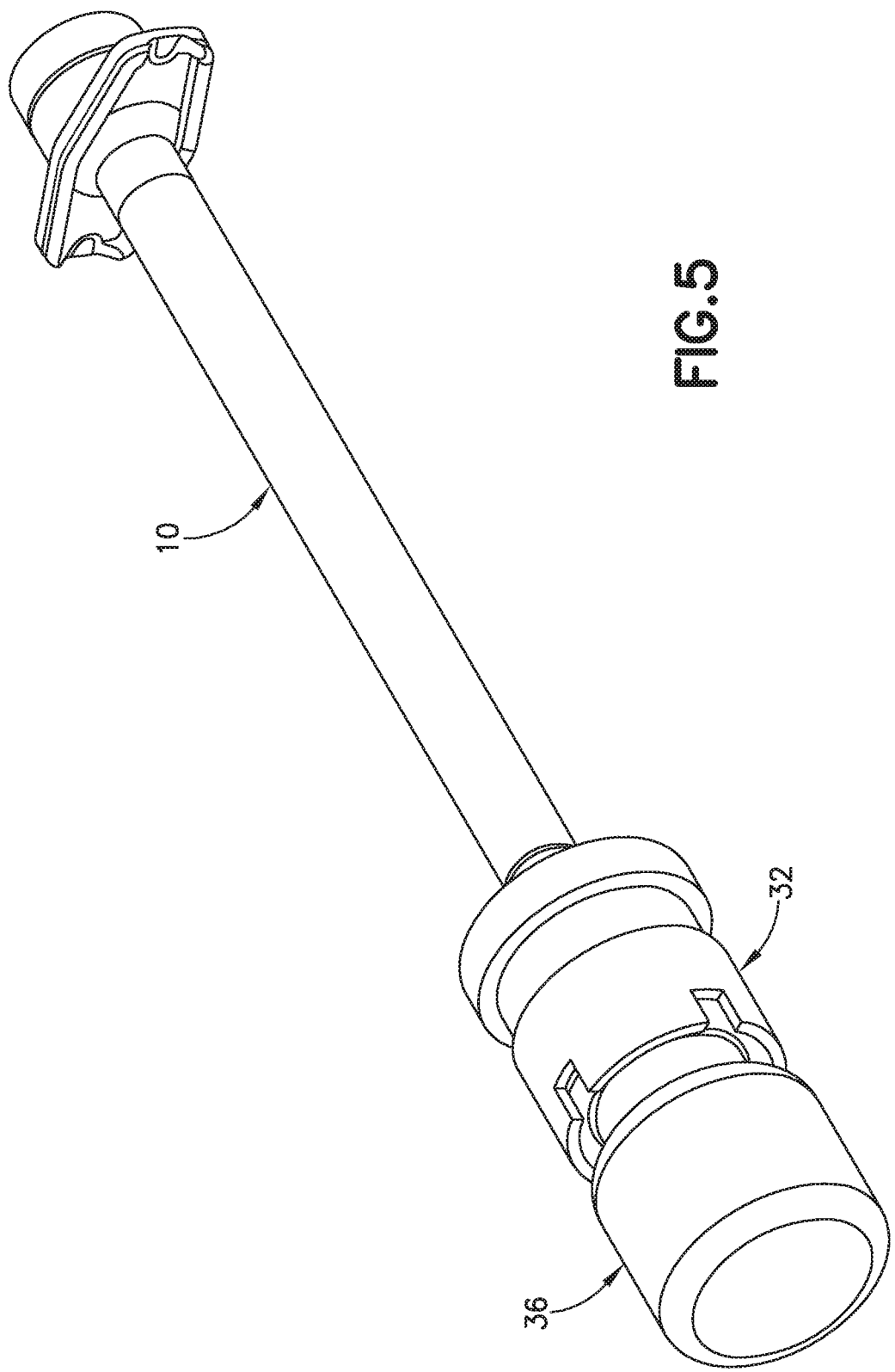

SYRINGE ASSEMBLY AND ADAPTER MEMBER

This application claims priority to U.S. provisional patent application Ser. No. 62/728,458, filed on Sep. 7, 2018, which is hereby incorporated by reference in its entirety.

FIELD OF THE INVENTION

The present invention is directed to an adapter member for connecting to a vial or container for filling and aspirating the syringe. The invention is also directed to an adapter member having a cavity for receiving a medication from a vial or container for use in filling a syringe and particularly a syringe having short needle length.

DESCRIPTION OF THE RELATED ART

The needle length of a syringe is often determined by the ability to fill the syringe from a vial or container that contains the medication. The vial typically has cap or septum that must be pierced by the needle to access the medication. As a result the needle requires a length to pierce the septum to access the medication. Needle lengths in the range of 4 mm to 5 mm are difficult to insert into a container or vial and aspirate due to the short length and the shape and dimension of the septum on the open end of the vial. The short length requires the needle to pierce septum in the vial in a straight line to ensure penetration and reduce the risk of the needle bending. The septum of a vial has thickness that varies across the width. The thickness of the septum is typically greater at the outer edges to engage the inner surface of the neck of the vial or container, A central portion of the septum has a thinner area that be pierced by the needle to fill the syringe.

The insertion of a needle into the skin of a patient is determined primarily on the features of the needle and not the features or structure of the needle support as disclosed in Needle Insertion Modeling; Identifiability and Limitations, L. Barbe, Biomedical Signal Processing and Control 2 (207) 191-198. Needle insertion into the skin of patient is generally classified into three phases that influence the injection depth. The first phase corresponds to the initial contact of the needle with the skin where the tissue deforms without puncturing the surface of the skin. A second phase refers to the puncture of the skin and the relaxation of the skin when the insertion force of the needle is stopped. The third phase is where the needle is extracted and pulls or stretches the skin outward as the needle is extracted.

Needle lengths, such as needles having a length of about 4 mm to 5 mm are adapted to inject a medication to a specified target depth in a subcutaneous region. The present invention provides a structure so that a needle can be consistently inserted to a desired target depth. Prior pen needles have the cannula supported on an axial post extending from the hub. The post forms a narrow portion and a relatively wider base that does not contact the skin during the injection. In other pen needles known in the art, a distal face of the hub placed against the injection site may be relatively large, and may be provided with a slight taper at the edge. The edge of the hub can engage the skin when the cannula is inserted at an angle relative to the surface of the skin of the patient.

Various injection devices have been produced where the supporting structure does not contact the skin during injection or extraction of the needle. Other devices have been proposed where the end face of the device is positioned to contact the surface of the skin to limit the depth of penetration into the patient.

Pen-injector delivery devices facilitate self-administration of parenteral medications. Pen needles are a component of needle-based injection systems and consist of a doubled ended cannula assembled into a plastic hub using adhesive. The hub has internal threads, which allow it to be attached to the pen-injector device. Pen needle attachment allows the proximal end of cannula to penetrate through the rubber septum of the medicament cartridge to create the fluid flow path. For many diabetics maintaining blood glucose control is achieved by performing multiple daily injections of insulin into the subcutaneous (SC) tissue using pen injector delivery devices developed to be a convenient, discreet alternative to the vial and syringe. Numerous pen injectors are commercially available in either disposable or multi-use configurations, each offering various patient-centric features. The distal pen needle cannula interfaces with the delivery site providing a conduit for delivery. Pen needle designs are intended to enable consistent delivery to the target tissue space, minimize leakage of injectate, and reduce pain/discomfort and site effects such as bleeding and bruising associated with the injection. The primary design features, needle length/gauge and hub face geometry, in conjunction with mechanics of the delivery system and injection technique, dictate injection success.

Injections may be performed in the intradermal region, the subcutaneous region and the intramuscular (IM) region of the skin. For many types of injectable medications, including insulin, the SC region is preferred for administering an injection. See, for example, Lo Presti, et al., Skin and subcutaneous thickness at injecting sites in children with diabetes: ultrasound findings and recommendations for giving injection, Pediatric Diabetes (2012).

While the prior devices are generally suitable for the intended use, there is a continuing need for improved devices for controlling the depth of penetration of a cannula for delivering a drug or medicament to a selected target area.

SUMMARY

The present invention is directed to syringe assembly and adapter member to assist in piercing the septum in a container, vial or other vessel that contains a medication and for filling and aspirating the syringe. In one embodiment, the syringe assembly is used in conjunction with an adapter where the adapter has a cavity for receiving an amount of the medication or other substance from the container or vial to assist in filling and aspirating the syringe.

The syringe assembly in one embodiment includes a syringe barrel and a needle hub coupled to the distal end of the syringe barrel. An adapter is provided for coupling to a container having a septum where the adapter cooperates with the syringe and needle for filling the syringe with a medication contained in the container.

The syringe assembly is primarily used with short needles having a length of about 4 mm to about 6 mm. Needles having a length of about 4 mm are desirable for certain uses, such as in the delivery of insulin where the 4 mm needle delivers the insulin to a desired depth in the patient. Filling 4 mm needle syringe requires insertion of the needle carefully through the septum of a container containing the insulin or other medication. The syringe assembly provides a mechanism where the contents of a container can be accessed in a manner that the syringe can be filled for needles of varying lengths. The syringe assembly provides a reduced occurrence of bending or damaging of the needle or the piercing of the septum in a location where the distal tip of the needle embeds in the septum and is unable to contact the contents of the vial or container.

The syringe assembly includes a syringe barrel with a needle where the syringe barrel cooperates with an adapter member that is coupled to a container. In one embodiment, the adapter member has a distal end formed with flexible legs. The legs can have at least one detent to engage the neck of the container. The legs flex outward to receive the neck of the container so that the container is coupled to the collar. The flexible legs have at least one and typically a plurality of ribs or detents to grip the neck of the container. The needle of the syringe passes through the adapter for filling the syringe.

The syringe barrel has a distal end with needle hub supporting a needle. The needle can have a length suitable for the intended use. In one embodiment, the needle has a length of about 4 mm. An adapter member is configured for coupling to the open end of a vial or container and for receiving the needle and needle hub. The adapter member in one embodiment has a cavity and a cannula in communication with the cavity. The cannula is configured to penetrate a closure of the container so that at least a portion of the substance in the container can be transferred to the cavity of the adapter. The cannula preferably has a length and orientation to pierce the septum of the container in a location where the contents of the container is accessible. The adapter has a proximal end configured for receiving the needle where the substance can be pulled into the syringe.

The syringe assembly in one embodiment has a coupling member on a distal end that couples to the proximal end of the adapter with the syringe needle positioned within the cavity of the adapter. The needle is inserted into the cavity of the adapter for filling the syringe for delivering the substance to the patient.

The adapter in one embodiment has a coupling mechanism for coupling with a container and a cannula for penetrating the container to access the contents. A cavity in the adapter receives a portion of the contents of the container where the contents can be accessed by the syringe. The adapter has a closure member where a syringe needle can pierce the closure member to access the cavity for filling the syringe.

The features are basically attained by providing an adapter for connecting to a container where the adapter includes a body having a cavity, a distal end configured for coupling to a container containing a substance, and a proximal open end opposite the distal end. A closure member is coupled to the proximal end of the body, where the closure member has a thickness where a syringe needle can pierce the closure member to access the cavity of the adapter. A cannula extends from the distal end of the body for accessing a substance within a container. In one embodiment, the adapter includes a vent mechanism to allow air to pass into the container to enable the contents to flow into the cavity of the adapter.

The features of the assembly are also provided by a container having a cavity for containing a substance where the container has an open end and a closure member coupled to the open end. An adapter has a body with a proximal end and a distal end. A cavity is formed in the adapter between the distal end and the proximal end. The proximal end of the adapter has a thickness where a syringe needle can pierce the adapter. A cannula extends from the distal end of the body where the cannula is configured for piercing the closure member on the container for delivering at least a portion of the substance of the container to the cavity of the body of the adapter.

A method is provided for filling a syringe using the syringe apparatus and adapter. The method comprises providing a syringe assembly comprising a syringe barrel having a proximal end and distal end, a needle hub coupled to the distal end of said syringe barrel. An adapter member is coupled to an open end of a container and has a cannula for piercing a septum on the container where the contents of the container are transferred to a cavity in the adapter. The needle of the needle hub is inserted through the open end of the adapter member where the needle enters the cavity of the adapter where the syringe can be filled with the substance from the container. The filled syringe then is separated from the adapter. The filled syringe is then ready for use, such as for delivering the substance to a patient.

These and other features of the invention will become apparent from the following detailed description of the invention, which in conjunction with the drawings disclose various embodiments of the invention.

BRIEF DESCRIPTION OF THE DRAWINGS

The following is a brief description of the drawings in which:

FIG. 4 is a bottom perspective view of the adapter member of FIG. 1;

FIG. 5 is a perspective view of the syringe assembly connected to the adapter member of FIG. 1;

DETAILED DESCRIPTION OF THE EMBODIMENTS

Figure 1:
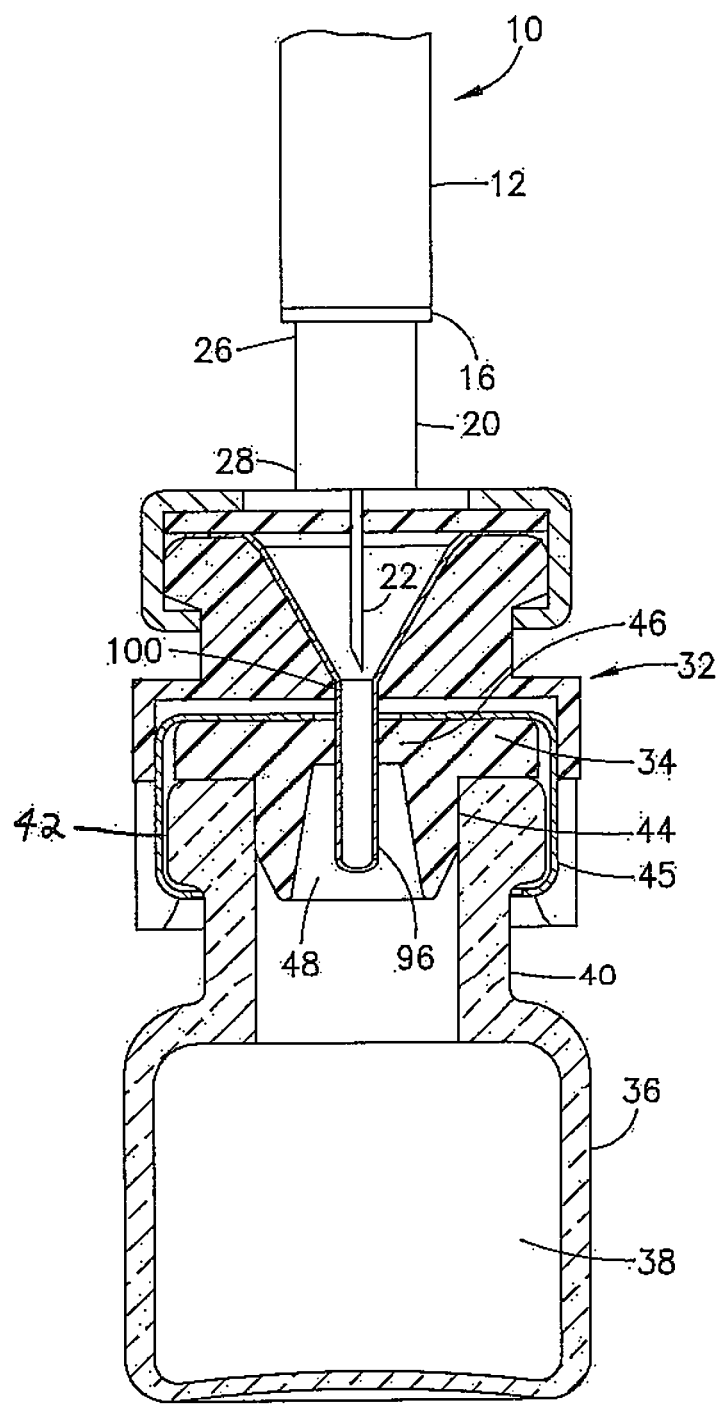
FIG. 1 is a cross section view of the adapter member for attaching to the container and for the syringe and needle while filling in one embodiment of the invention.
Figure 3:
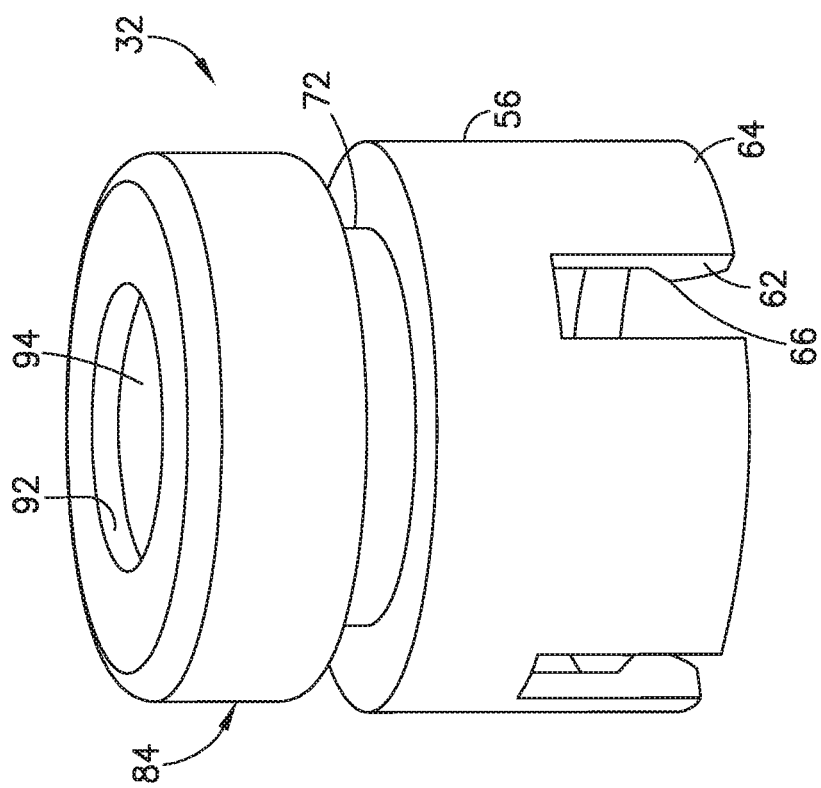
FIG. 3 is a perspective view of the adapter member in the embodiment of FIG. 1.

The syringe assembly of the invention refers to a syringe having a needle or cannula that can be used for delivering or injecting a medication or other substance into a patient. The terms needle and cannula are used herein interchangeably to refer to a thin tubular member having a sharp end for insertion into an injection site on a subject. A distal direction is in the direction toward the injection site, and the proximal direction is the opposite direction. The axial direction refers to a direction along or parallel to the longitudinal axis of the needle and the needle hub and the radial direction refers to a direction perpendicular to the axial direction. The embodiments of the assembly as described can be combined with features of other embodiments as long as they do not contradict one another.

The intradermal layer in adults generally has a thickness of around 2 to 3 mm, so that intradermal injection depth is in a range of up to about 3 mm as measured from the outer surface of the skin. The thickness of the subcutaneous layer varies depending on the age of the patient, gender, body mass index (BMI), and the part of the body where the injection is administered. The subcutaneous region has an average thickness of about 7 mm to about 15 mm. Insulin is preferably delivered to the subcutaneous region. Insulin injections are commonly injected using a 4 mm needle.

The syringe assembly is suitable for use in a method for injections and for injecting a medication or drug to a patient. The description of the embodiments is not to be deemed as limiting the invention. The disclosure is intended to enable the artisan of ordinary skill to practice variants of the invention described without departing from the scope of the invention. Numerical limitations herein, in the specification and in the claims, are understood to be limited by the modifier "about," such that minor departures yielding equivalent results is within the scope of the invention. The term substantially refers to mostly but not necessarily entirely. Features or dependent claim limitations disclosed in connection with one embodiment or independent claim may be combined in another embodiment or with a different independent claim without departing from the scope of the invention.

The invention is directed to a syringe assembly that is configured for connecting to a container such as a container or other vessel containing a medication to facilitate filling and aspirating a syringe. In the description of the embodiments, the term vial and container can be used interchangeably and define a vessel containing a medication, such as insulin. The vial refers to a container or vessel that contains and stores a medication and can have various shapes, sizes and volumes. Referring to the drawings, the syringe assembly 10 includes a syringe barrel 12 having a proximal end and a distal end 16. The proximal end receives a movable plunger and stopper for dispensing the substance contained in the syringe assembly in a typical manner. An adapter member 32 connects to a container 36 or other vessel containing a medication, drug or other pharmaceutical for aspirating the syringe.

A needle hub 20 is coupled to the distal end 16 of the syringe barrel 12 as shown in FIG. 1. The needle hub 20 includes a needle 22 extending axially from the needle hub. The needle hub 20 is configured for coupling to the distal end of the syringe barrel 12. The needle hub 20 has a substantially cylindrical body with a proximal end 26. A distal end 28 projects axially outwardly for contacting the surface of the skin of the patient during use.

The needle 22 in the embodiment shown has a length of about 4-6 mm extending from the distal end of the syringe although the exposed length of the needle can vary depending on the particular needs of the syringe apparatus. The syringe assembly as described is primarily intended for use with shorter needle lengths, such about 4 mm that can be difficult to pierce a septum of a container compared to longer needle lengths. The shorter needle lengths can be difficult to pierce the septum in a straight line to fill the syringe. The needle 22 has a sharp distal tip and a lumen for communicating with the syringe barrel in a typical manner. The needle 22 extends from the needle hub a distance to provide an exposed length of the needle for injecting the medication to a desired depth into the patient. In the embodiment shown, the exposed length of the needle is about 4 mm although the length can vary as needed.

Referring to FIG. 1, distal end 28 of the needle hub 20 and needle 22 are configured for mating with the adapter 32 for filling the syringe with the contents of the container 36 or other container that contains a medication, such as insulin. As shown in FIG. 1, the container 36 defines a container for storing the medication until ready for use. The term vial and container are used interchangeably to refer to a container, bottle or other storage vessel used for storing a medication. The container 36 has an internal cavity 38 and a neck 40 with an outwardly projecting annular lip 42. The septum 34 fits into the open end of the container 36 to seal the container 36. The septum 34 has an annular shaped collar 44 that extends into the neck 40 for coupling to the container typically by a friction fit. The annular shaped collar 44 forms an internal space 48 communicating with the cavity of the container. A top wall 46 having a flat outer face contacts the top end of the neck 40. The top wall 46 has a thickness to enable a needle to pierce the septum 34 and extend into the internal space of the collar 44 for recovering the medication in the container. A cap 45 is typically provided over the septum to secure the septum to the container. The cap 45 can be a metal film press fitted or crimped over the septum to wrap around the lip of the container as shown. A central open area of the top face of the cap exposes the top wall of the septum 34 for enabling a needle or a cannula to pierce the septum.

The needle hub 20 in the embodiment shown has a substantially flat distal end that is able to contact the adapter while filling the syringe and to contact the skin of the patient during the injection to limit the depth of penetration of the needle into the skin of the patient. Needles having a length of 4 mm or less must pierce the septum in the thin portion of the top wall, which is typically the center of the septum to be able to penetrate the cavity containing the medication. The adapter member provides a mechanism for receiving a portion of the substance from the container for filling the syringe.

The adapter 32 in the embodiment of FIGS. 1-5 is configured to attach to the open end of the container 36 and to cooperate with the syringe on the needle hub. The adapter 32 has an open top end 50 and an open bottom end 52 shown in FIG. 2. The open bottom end 52 has an internal cavity with a shape and dimension for coupling with the top end of the container 36. The adapter 32 is shown as a one-piece integrally formed member. The adapter can made of a suitable material that is able to couple to the container or container while the needle penetrates the septum on the container. The adapter 32 can be made of molded plastic material that is sufficiently flexible to attach to the container.

The adapter 32 has a substantially circular shape with a body 54 having a depending collar 56 forming the open bottom end 52. The collar 56 has a substantially cylindrical shape with an outer surface 58 and an inner surface 60. Notches 62 are cut in the bottom edge to form legs 64 shown in FIGS. 2-4. The legs 64 have an inwardly extending detent in the form of a lip 66 surrounding the open bottom end 52 shown in FIG. 2. The lip 66 has an inclined distal surface 68 for sliding over the lip 42 of the container 36 and an inclined proximal surface 70 for enabling the separation of the adapter from the lip of the container. The legs 64 are sufficiently resilient to snap over the lip of the container for attaching the adapter to the container and for separating the adapter from the container after use.

Figure 2:
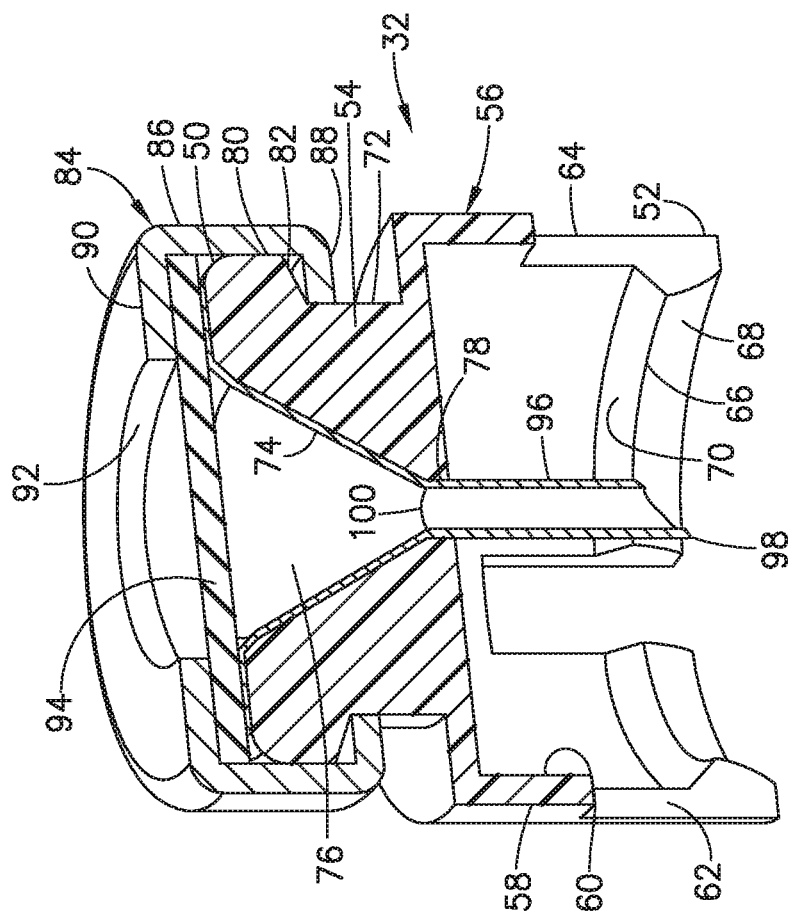
FIG. 2 is a cross-sectional view of the adapter member of FIG. 1.

The outer surface of the body 54 has an annular recess 72 shown in FIG. 2 to assist the user in manipulating the adapter when attaching to and separating from the container and to form an annular shaped lip 80 having a radially extending bottom edge 82. The adapter 32 has an inclined surface 74 in the top end 50 forming a cavity 76 in the adapter 32. In the embodiment shown, the surface 74 is in the form of a conical shaped surface having an open top end and converging to an opening 78 in the bottom end of the adapter 32. The cavity 76 typically has a volume corresponding to the desired dosage that is to be loaded into the syringe.

A closure member 84 is coupled to the top end 50 of the adapter 32 to close the open end of the adapter and enclose the cavity 76. The closure member 84 has an outer wall 86 with an inwardly extending flange 88 for coupling to the lip 80 of the adapter 32. A top wall 90 of the closure member 84 has a central open area 92. A seal 94 is positioned between the inner surface of the top wall 90 and the top end of the adapter 32 as shown in FIG. 1 and FIG. 2 to close and seal the cavity 76. The seal 94 is made of suitable material that is able to form a fluid seal against the open top end of the adapter and can be penetrated or pierced by a needle of a syringe. The seal 94 in the embodiment shown is a substantially flat member having an outer dimension to fit within the closure member 84, form a seal with the top end of the adapter, and be accessible through the open area 92 in the closure member. The seal 94 can be made of a plastic or rubber material and forms a septum that can be penetrated or pierced by a syringe needle.

A cannula 96 extends from the open bottom end of the adapter 32 and communicates with the cavity 76. The cannula 96 in the embodiment shown has a tubular configuration with a sharpened distal tip 98 shown in FIG. 2. A proximal end 100 has an outer diameter corresponding to the inner diameter of the opening 78 at the bottom end of the adapter and forms a fluid tight seal with the open bottom end of the container. The cannula 96 has an axial length sufficient to pierce the septum of a container 36 to access the contents. A lumen extends through the cannula between the proximal end and the distal end to carry the substance from the container to the cavity 76. In the embodiment shown, the cannula 96 is formed as a separate funnel shaped member where the conical portion complements the conical shaped surface of the adapter. The cannula 96 is formed from the outlet spout of the funnel shaped member. The cannula 96 has a dimension complementing an opening in the adapter where the funnel shaped member is attached by a friction fit, adhesive or other suitable coupling mechanism as shown in FIGS. 1 and 2.

During use of the syringe and adapter, the adapter 32 attaches to the open end of the container as shown in FIGS. 1 and 5 by sliding the open end of the adapter over the lip of the container. The lip 66 on the legs 64 of the collar 56 snap onto the neck 40 of the container as shown in FIG. 1 and FIG. 5. The collar 56 of the adapter 32 in the embodiment shown has an inner diameter corresponding to the outer diameter of the open end of the container 36 and an axial length where the bottom face of the body 54 contacts the top face of the septum 34. The cannula 96 is pressed into the seal 94 where the cannula pierces the seal to access the cavity and the contents of the container as shown in FIG. 1. At least a portion of the contents of the container is transferred to the cavity 76 of the adapter. The adapter attached to the container can be inverted to transfer the contents of the container through the cannula 96 to flow into the cavity 76 by gravity, a pressure formed in the cavity of the container, or by a reduced pressure formed in the cavity of the adapter. The pressure in the container can be produced by aspirating the syringe. The reduced pressure can be formed by retracting the plunger from the syringe.

The syringe needle 22 pierces the seal 94 and is inserted in the open top end of the adapter as shown in FIG. 5 where the needle extends into the cavity 76 as shown in FIG. 1. The syringe, adapter, and container can then be inverted where the plunger of the syringe can be withdrawn to draw the contents of the container into the cavity where the syringe can pull the medication from the cavity into the syringe barrel. The syringe needle is withdrawn from the adapter after filling the syringe. The syringe is then ready for delivering the medication to the patient.

FIGS. 6-9 show another embodiment where the adapter 104 is similar to the previous embodiment where the adapter has a collar 106 with legs 108 for coupling to the open end of a container 110. As in the previous embodiment, an inwardly extending lip 112 is formed on the legs 108. The adapter 104 is configured for connecting to the container 110 and cooperating with the syringe and guide member as in the previous embodiment. A body 114 of the adapter 104 has a substantially cylindrical shaped wall forming a cylindrical shaped cavity 116. The adapter 104 is similar to the adapter 32 of the previous embodiment except for the cylindrical shaped cavity 116. The top end of the adapter 104 includes a closure member 105 and seal 107 forming a septum as in the previous embodiment. The adapter 104 is used in the same manner as the embodiment of FIGS. 1-5 by attaching the adapter to the container where the cannula 118 on the adapter pierces the septum 119 of the container where the medication from the container can be transferred to the cavity 116 for filling the syringe by inserting the syringe needle into the cavity 116. In the embodiment shown, the cannula 118 is a separate member that can be attached to the bottom wall of the adapter or can be inserted into the opening in the bottom wall and retained by a friction fit or an adhesive.

Figure 11:
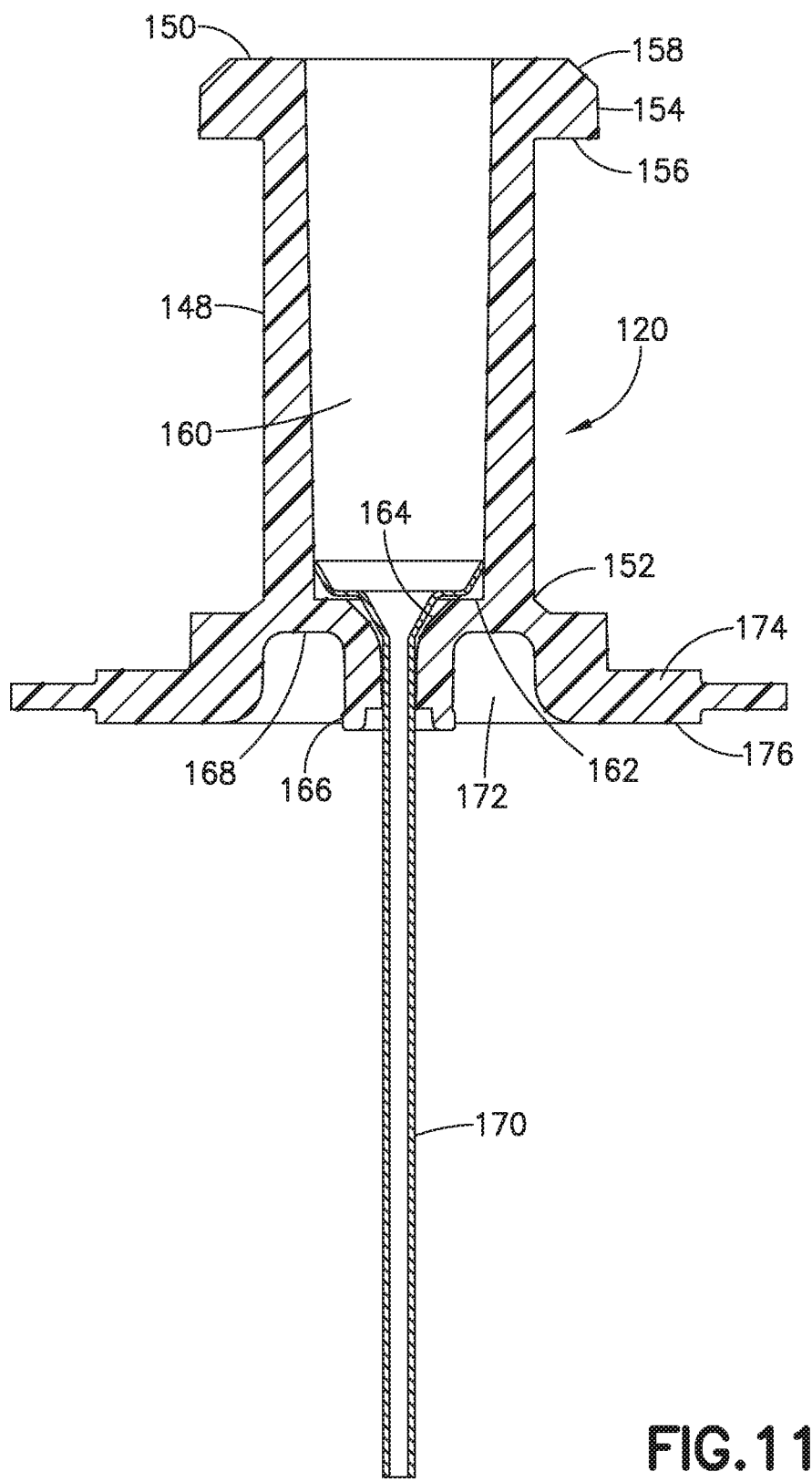
FIG. 11 is a cross-sectional view of the adapter in a further embodiment for use with the syringe of FIG. 10.
Figure 12:
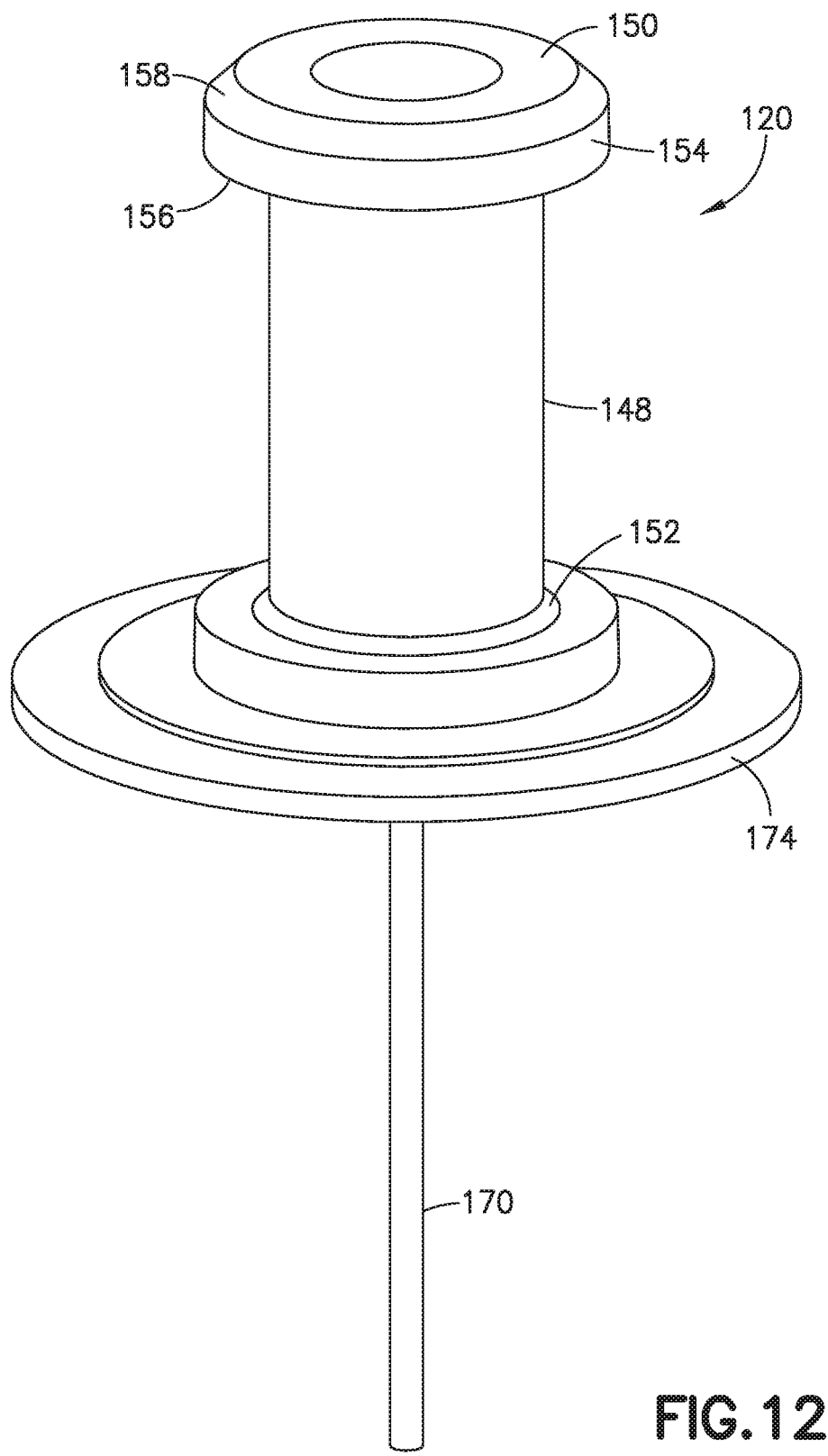
FIG. 12 is a perspective view of the adapter of FIG. 11.
Figure 13:
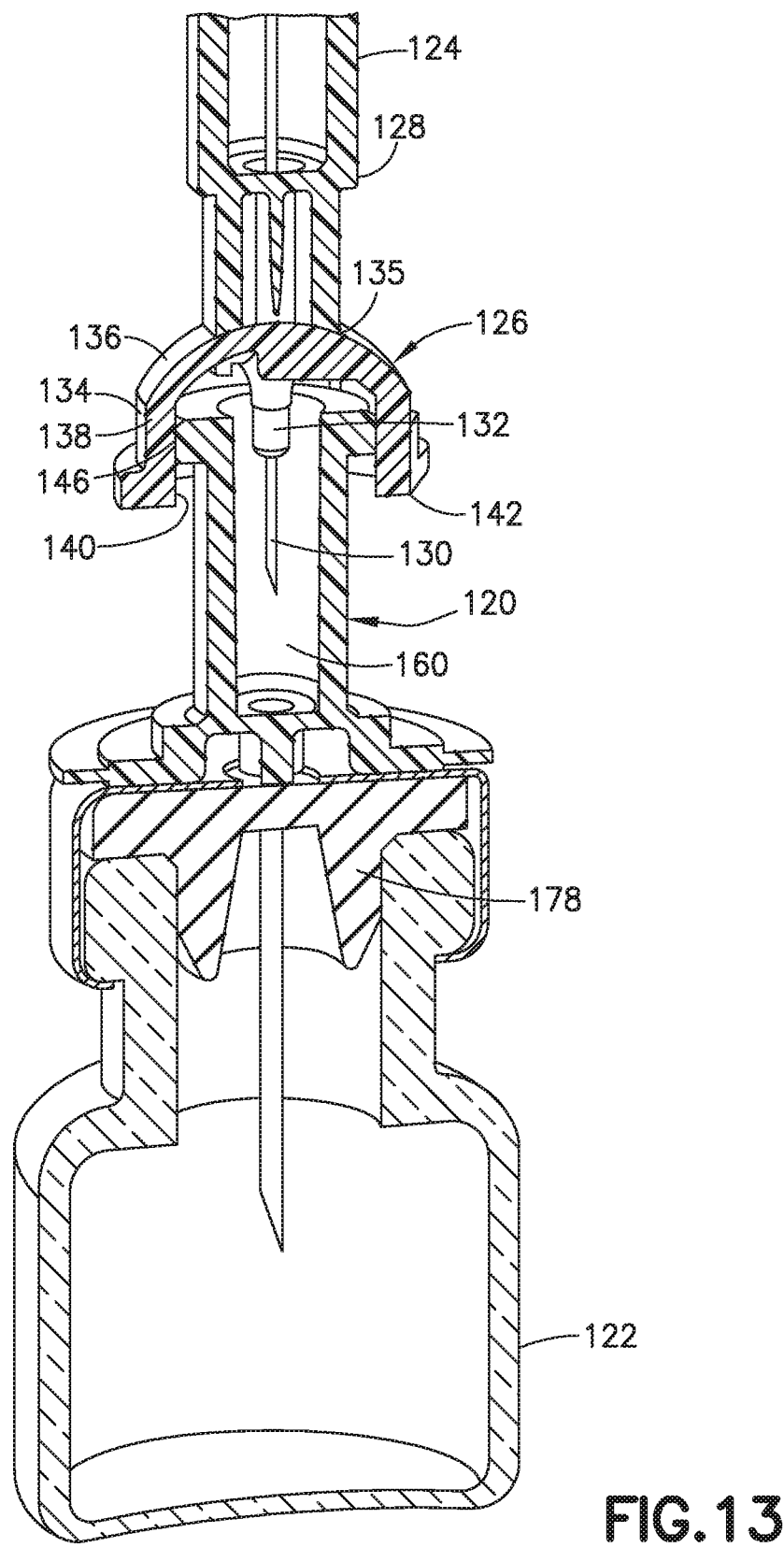
FIG. 13 is a cross-sectional view showing the syringe coupled to the adapter member of FIG. 10.
Figure 14:
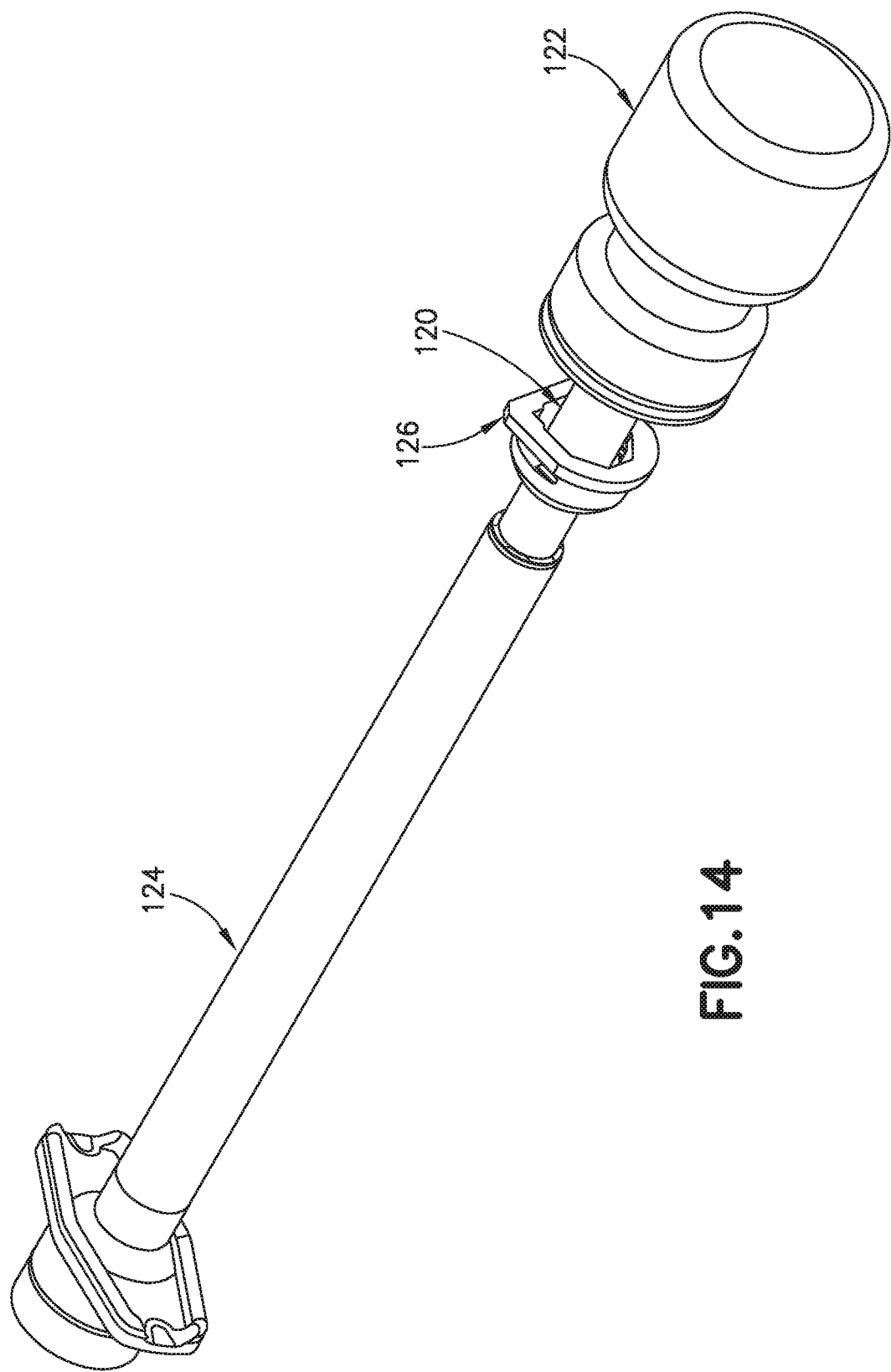
FIG. 14 is a perspective view of the syringe assembly connected to the adapter member of FIG. 11.

FIGS. 10-14 show another embodiment of the adapter 120 and syringe for coupling to the open end of the container in a manner similar to the previous embodiments. In the embodiment of FIGS. 10-14, adapter 120 is configured for attaching a container 122. The syringe 124 is configured for coupling to the adapter 120 and includes a closure member for the adapter that functions as a coupling member 126 for coupling with the adapter 120 as shown in FIG. 13.

Figure 10:
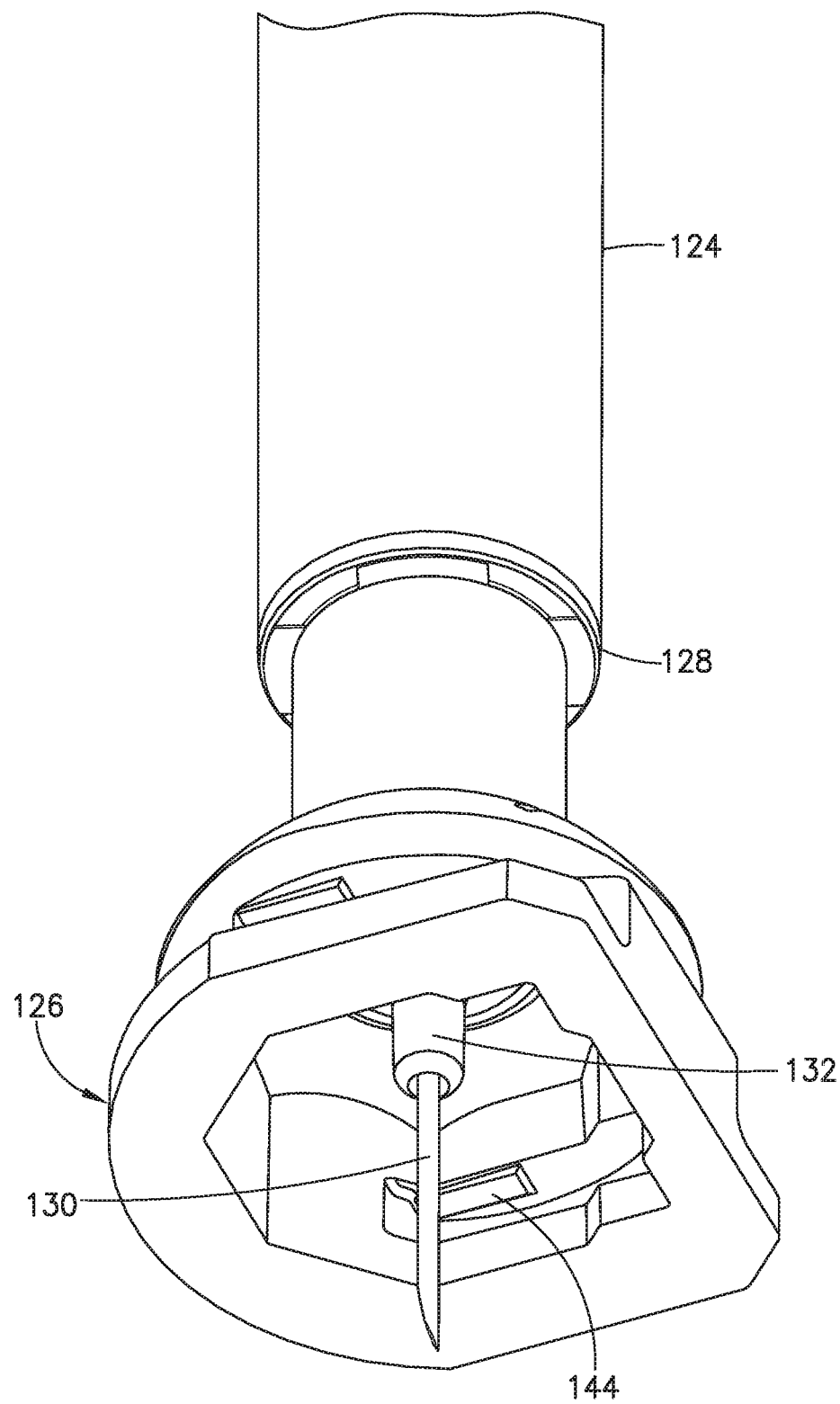
FIG. 10 is a bottom perspective view of the syringe and coupling member in another embodiment.

The coupling member 126 of the syringe as shown in FIGS. 10 and 13 can be connected to the distal end 128 of the syringe 124 and surrounds a needle 130 and needle hub 132 where the needle 130 extends from the coupling member a suitable distance for delivering the substance to the patient. The adapter 126 can be formed as a separate member that attached to the distal end of the syringe or needle hub, or can be formed as a one piece assembly with the syringe and needle hub. In other embodiments, the coupling member 126 is attached to the adapter 120 and the needle is then inserted into an opening in the adapter. The needle 130 has an axial length greater than the axial length of the coupling member 126 as shown in FIG. 13 and has an exposed length suitable for delivering a medication to a patient. The coupling member 126 has a body 134 with an opening 135 at a proximal end 136 coupled to the distal end 128 of the syringe 124. A depending collar 138 extends from the body 134 having an inner surface 140 forming a cavity in the collar 138. The collar 138 has an axial length for coupling with the proximal end of the adapter 120 and defining a distal end 142 of the coupling member 126. As shown in FIG. 10, slots 144 are formed on opposite sides of the collar 138 forming annular recesses 146 on the inner surface 140 for mating with the adapter 120.

The adapter 120 as shown in FIGS. 11 and 12 have a substantially cylindrical shaped body 148 with an open proximal end 150 and a distal end 152. The open proximal end 150 includes an annular shaped lip 154 extending radially outward. The annular lip 154 has a bottom face 156 extending substantially perpendicular to the longitudinal axis of the adapter and a chamfered top edge 158 for sliding into the open end of the coupling member 126. The annular lip 154 has a diameter complementing the inner dimension of the coupling member 126 and the recesses 146 of the coupling member for connecting the coupling member to the adapter 120. The annular lip 154 is able to snap into recesses 146 while filling the syringe and can be removed after filling the syringe.

The cylindrical shaped body 148 forms an internal cavity 160 with a diameter and length to receive the needle 130 as shown in FIG. 13. The distal end 152 of the body 148 has a bottom wall 162 closing the cavity 160 where the bottom wall 162 is formed with an opening 164 extending axially through the bottom wall 162. A hob 166 extends axially from the bottom face 168 of the bottom wall 162 for supporting a cannula 170 that is received in the opening 164 and attached to the bottom wall 162. The cannula 170 has a lumen extending between a distal end and a proximal end for conveying liquids to the cavity 160. In the embodiment shown, an annular recess 172 is formed around the hub 166. The cannula 170 is shown with a funnel shaped portion having a shape complementing the shape of the opening 164 and the bottom surface of the adapter. The cannula 170 is attached to the adapter 120 by a friction fit or by an adhesive.

The bottom wall 162 has an outwardly extending radial flange 174 with a bottom face 176 as shown in FIG. 11. In the embodiment shown, the bottom face 176 has a shape and dimension complementing the top face of the cap on the container 122. The bottom face 176 typically has a substantially flat surface for mating with the top face of the cap on the container as shown in FIG. 13. The bottom wall 162 can be made of flexible or resilient material to conform to the face of the cap of the container.

The cannula 170 of the adapter 120 is inserted through the septum 178 on the container 122 as shown in FIG. 13 to access the medication or other substance in the container 122. The cannula 170 has a length and strength sufficient to penetrate the septum so the open end of the cannula 170 is oriented within the cavity of the container for accessing the medication. The coupling member 126 of the syringe 124 is connected to the adapter 120 before or after the adapter is connected to the container. The collar 138 of the adapter body 134 snaps onto the lip 154 of the adapter 120 where the needle 130 is oriented within the cavity 160. The contents of the container are transferred to the cavity 160 of the adapter 120 by inverting the container and retracting the plunger from the syringe to fill the syringe. The syringe needle and syringe are withdrawn and separated from the adapter where the filled syringe is ready for use. In one embodiment, the coupling member 126 can be separated from the syringe prior to use for injecting the medication into the patient.

Figure 6:
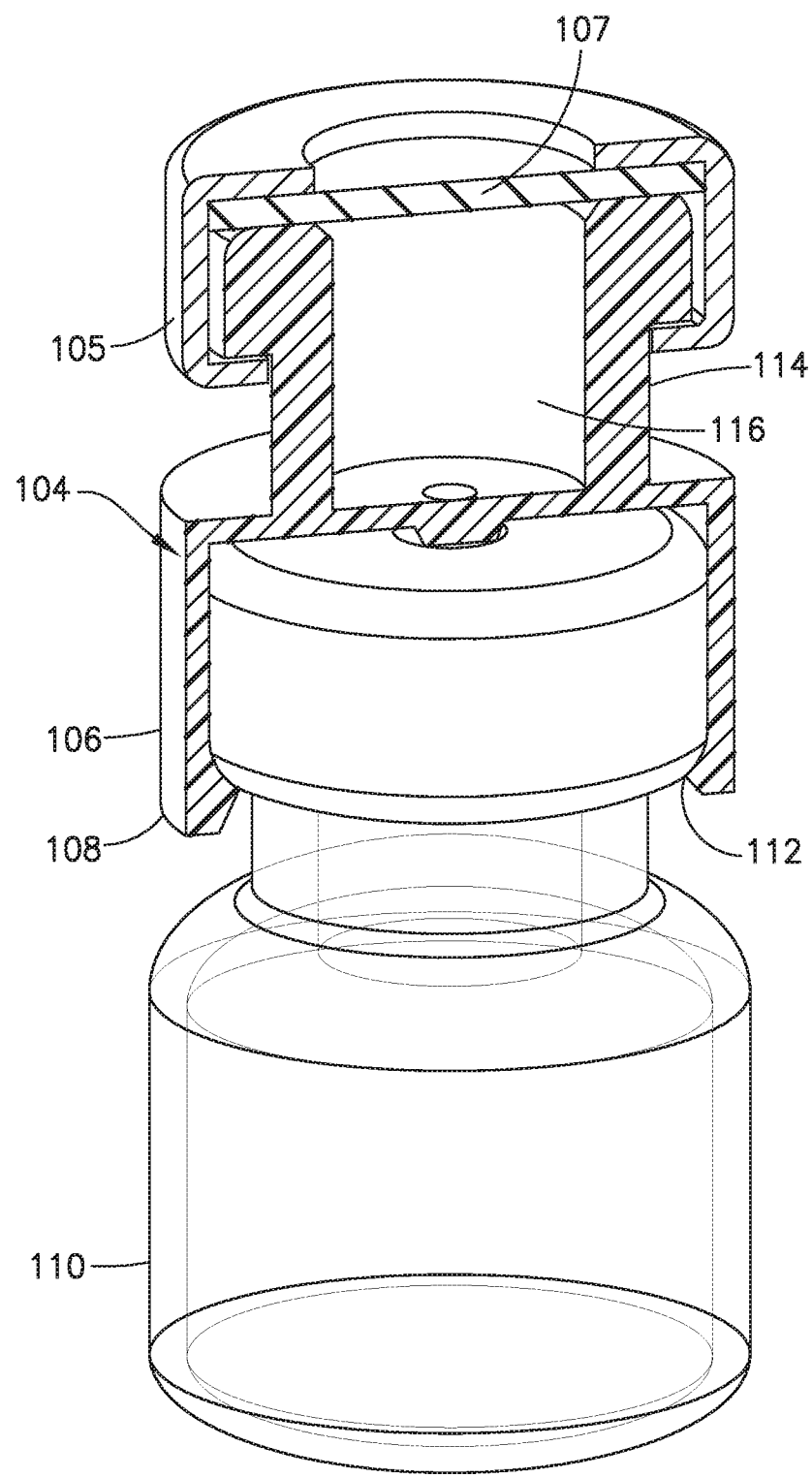
FIG. 6 is a cross-sectional view of the adapter member and container in another embodiment.
Figure 7:
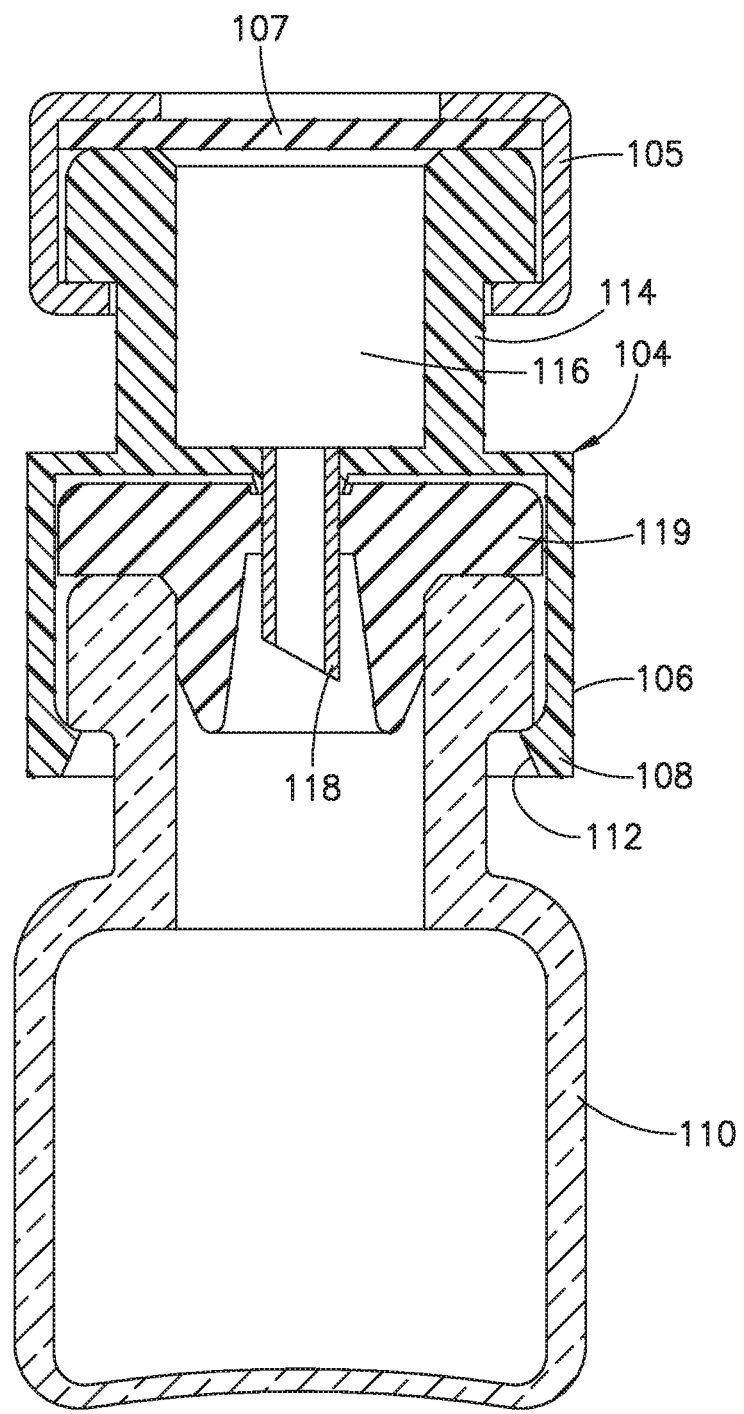
FIG. 7 is a cross-sectional view of the adapter member and container in the embodiment of FIG. 6.
Figure 9:
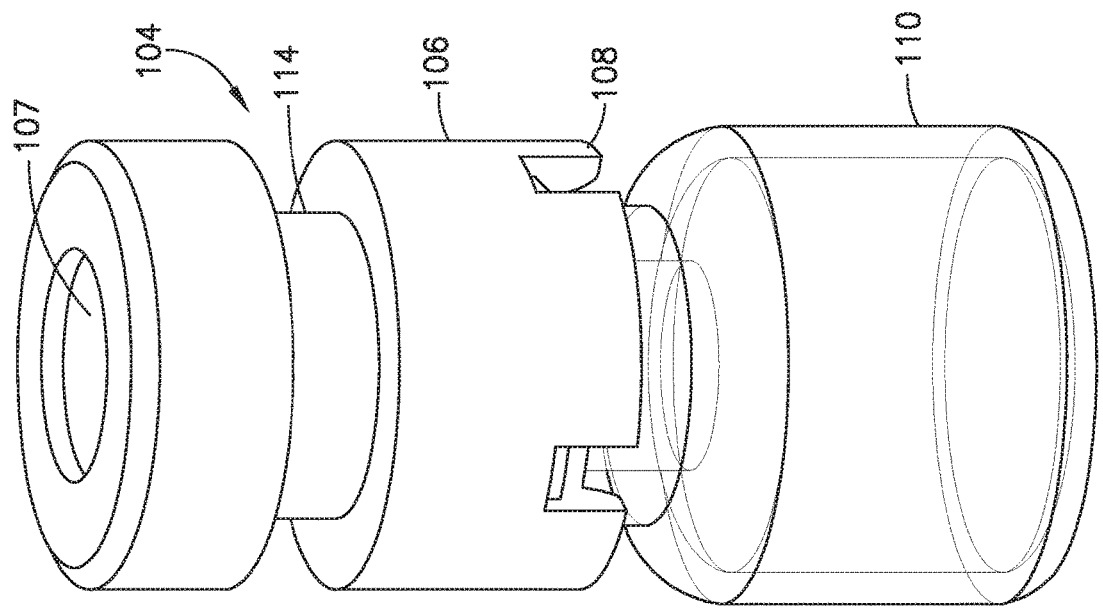
FIG. 9 is a perspective view of the adapter member and container of the embodiment of FIG. 6.
Figure 8:
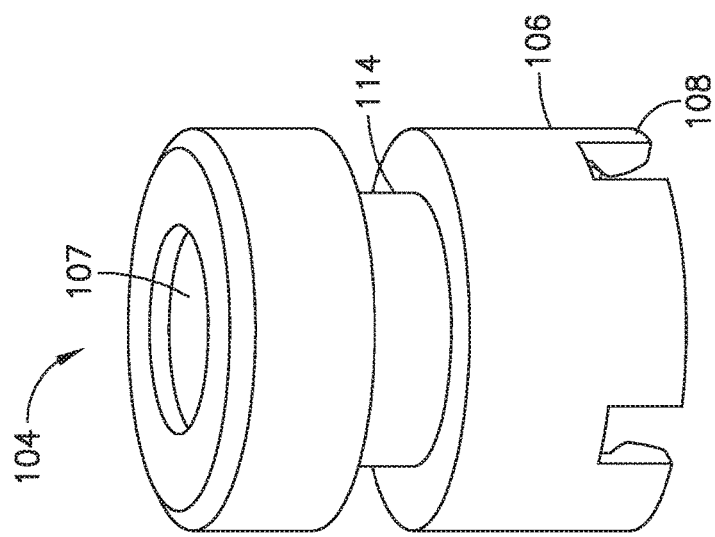
FIG. 8 is a perspective view of the adapter member of the embodiment of FIG. 6.
Figure 15:
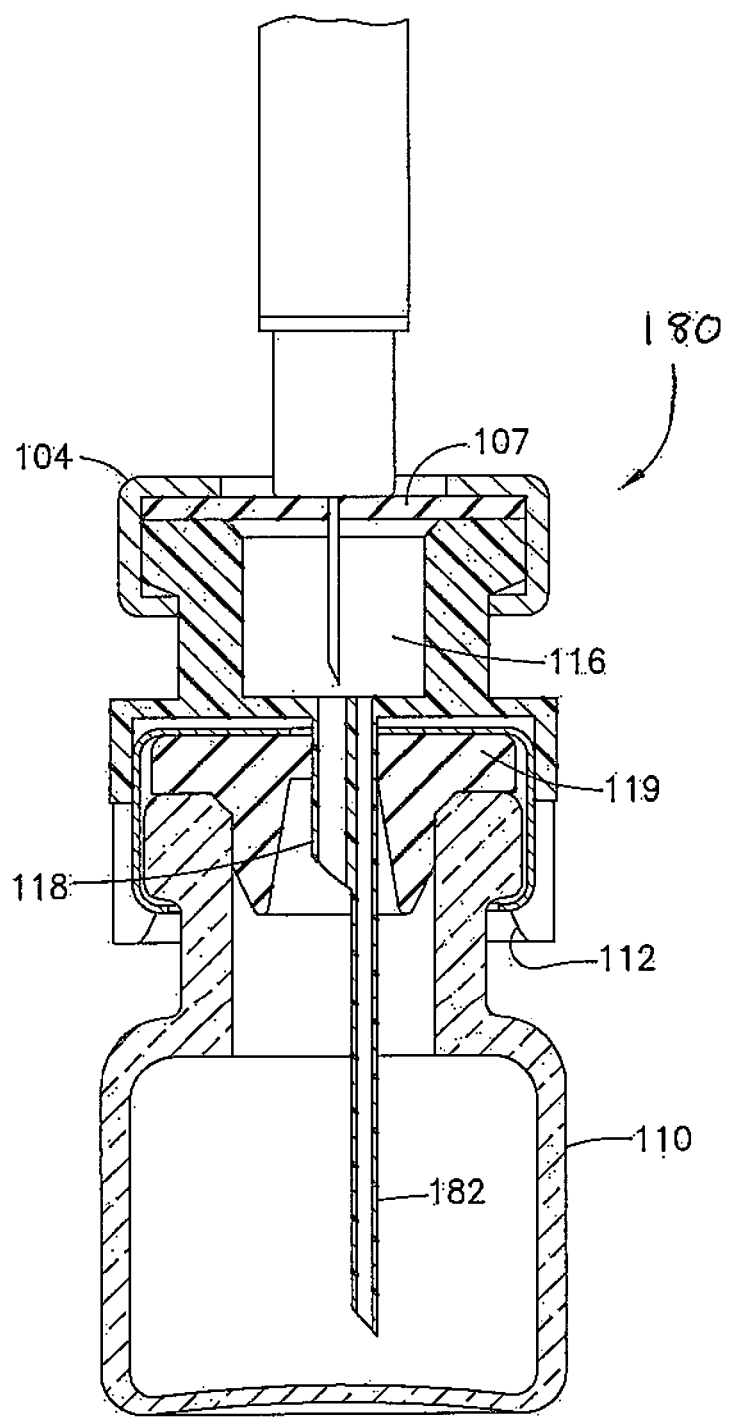
FIG. 15 is cross-sectional view of another embodiment of the adapter.

In another embodiment shown in FIG. 15, the adapter 180 is substantially the same as the embodiment of FIGS. 6-8 so that similar elements are identified by the same reference number. The adapter 180 of FIG. 15 includes a second cannula 182 forming a vent to allow air to pass between the cavity of the adapter and the container to equalize the pressure between them and enable to the contents of the container to flow into the cavity of the adapter. In the embodiment shown, the venting cannula 182 has an axial length greater than the cannula 118 to extend into the container a distance greater than the cannula 118. By inverting the container and adapter 180, the air in the cavity of the adapter can pass through the lumen of the cannula 182 to vent the cavity of the adapter 180 where the contents of the container can flow through the lumen of the cannula 118 into the adapter where the contents can be loaded into the syringe.

The foregoing embodiments and advantages are exemplary and are not intended to be construed as limiting the scope of the invention. The description of alternative embodiments are intended to be illustrative, and not to limit the scope of the present invention. Various modifications, alternatives, and variations will be apparent to those skilled in the art, and are intended to fall within the scope of the invention. It is particularly noted that the features of different embodiments and claims may be combined with each other as long as they do not contradict each other. Accordingly all such modifications are intended to be included within the scope of this invention as defined in the appended claims and their equivalents.

The invention claimed is:

1. A container assembly comprising: a container having a cavity for containing a substance, said container having an open end and a closure member coupled to said open end of said container; an adapter having a body with a proximal end and a distal end, a cavity oriented between said proximal end and said distal end, said proximal end configured where a syringe needle can be received in said cavity of said body, and said distal end configured for mating with said open end of said container; and a first cannula extending from said distal end of said body and having an open end communicating with said cavity of said adapter, said first cannula configured for piercing said closure member on said container for transferring at least a portion of the substance in said container to said cavity of said body, and a second cannula extending from said distal end of said body and having an open proximal end directly communicating with a distal end of said cavity of said adapter and being configured for venting said cavity.

2. The container assembly of claim 1, wherein said closure member comprises a septum received in said open end of said container.

3. The container assembly of claim 2, wherein said first cannula has a lumen with a proximal end in communication with said cavity of said body, and a distal end configured for piercing said septum of said container.

4. The container assembly of claim 3, wherein said body has a collar extending from said distal end, said collar having an open distal end for receiving the open end of said container.

5. The container assembly of claim 4, wherein said collar surrounds said first cannula, and where said collar has an inner surface with a coupling member for coupling to the container.

6. The container assembly of claim 5, wherein said coupling member on said collar comprises a detent projecting radially inward with respect to said collar.

7. The container assembly of claim 1, further comprising a closure member coupled to said proximal end of said adapter, said closure member having a thickness where a syringe needle can pierce said closure member to access the cavity of said adapter.

8. The container assembly of claim 7, wherein said closure member coupled to said proximal end of said adapter includes a septum that can be pierced by the syringe needle.

9. The container assembly of claim 1, wherein said second cannula has a length greater than said first cannula.

10. A syringe assembly comprising: a syringe barrel having a proximal end and distal end, and a syringe needle extending from said distal end; and an adapter configured for coupling to an open end of a container that contains a substance, said adapter having: a cavity; a proximal end with a closure member; a distal end, where said closure member can be pierced by said syringe needle to access said cavity; a first cannula extending from said distal end of said adapter and configured for piercing a septum on said container containing said substance; and a second cannula extending from said distal end of said adapter, wherein said first cannula and said second cannula are in direct communication with said cavity.

11. The syringe assembly according to claim 10, wherein said proximal end of said adapter has a closure member with a septum, where said septum can be pierced by said syringe needle for accessing said cavity of said adapter.

12. The syringe assembly according to claim 10, wherein said second cannula has a length greater than said first cannula.

* * * * *